(12) United States Patent
Spartz

(10) Patent No.: US 7,735,452 B2
(45) Date of Patent: Jun. 15, 2010

(54) SENSOR FOR PULSED DEPOSITION MONITORING AND CONTROL

(75) Inventor: Martin Spartz, Ellington, CT (US)

(73) Assignee: MKS Instruments, Inc., Wilmington, MA (US)

( * ) Notice: Subject to any disclaimer, the term of this patent is extended or adjusted under 35 U.S.C. 154(b) by 187 days.

(21) Appl. No.: 11/177,835

(22) Filed: Jul. 8, 2005

(65) Prior Publication Data
US 2007/0022951 A1 Feb. 1, 2007

(51) Int. Cl.
B05C 11/00 (2006.01)
(52) U.S. Cl. ..................................................... 118/688
(58) Field of Classification Search ................. 118/688
See application file for complete search history.

(56) References Cited

U.S. PATENT DOCUMENTS

| | | | |
|---|---|---|---|
| 5,196,784 A * | 3/1993 | Estes, Jr. ................. | 324/117 R |
| 5,550,636 A * | 8/1996 | Hagans et al. ............... | 356/437 |
| 5,851,842 A * | 12/1998 | Katsumata et al. ............ | 438/9 |
| 6,028,312 A * | 2/2000 | Wadsworth et al. ......... | 250/351 |
| 2003/0143747 A1 | 7/2003 | Bondestam et al. | |
| 2003/0200924 A1 * | 10/2003 | Ko et al. ..................... | 118/715 |
| 2003/0219528 A1 * | 11/2003 | Carpenter et al. ............. | 427/8 |
| 2004/0007180 A1 | 1/2004 | Yamasaki et al. | |
| 2005/0069632 A1 | 3/2005 | Yamasaki et al. | |
| 2005/0069641 A1 | 3/2005 | Matsuda et al. | |
| 2005/0095859 A1 * | 5/2005 | Chen et al. .................. | 438/689 |

FOREIGN PATENT DOCUMENTS

| WO | WO 2004/010462 A2 | 1/2004 |
|---|---|---|
| WO | WO 2004/088415 A2 | 10/2004 |
| WO | WO 2005/003406 A2 | 10/2005 |
| WO | WO 2005/103328 A1 | 11/2005 |
| WO | WO 2006/065426 A2 | 6/2006 |

OTHER PUBLICATIONS

"Handbook of Modern Analytical Instruments", By Raghbir Singh Khandpur, 1981, TAB Books Inc.*
PCT International Search Report for related PCT Application No. PCT/US2006/025338 (5 pages).
PCT Written Opinion of the International Searching Authority for related PCT Application No. PCT/US2006/025338 (7 pages).

* cited by examiner

Primary Examiner—Ram N Kackar
Assistant Examiner—Keath T Chen
(74) Attorney, Agent, or Firm—McDermott Will & Emery LLP

(57) ABSTRACT

Delivery of gas by a pulsed gas delivery device is monitored using a sensor. The sensor may include a source that generates radiation at a spectral range that includes an absorption frequency of the gas being delivered. The radiation is transmitted through a receptacle into which the delivered gas has been received. A detector detects the intensity of the radiation that reaches the detector from the source after transmission through the gas in the receptacle. A controller measures a precise quantity of the gas that was delivered by the gas delivery device, by determining from the detected intensity the amount of the radiation that was absorbed by the gas in the receptacle. The controller monitors in real time the delivery of the gas, by adaptively adjusting the quantity of gas being delivered to a desired quantity. The sensor and controller can also monitor for failures or for out-of-specification behavior of the gas delivery device.

23 Claims, 3 Drawing Sheets

SENSOR FOR PULSED DEPOSITION MONITORING AND CONTROL

CROSS-REFERENCE TO RELATED APPLICATIONS

The present application is related to application Ser. No. 10/822,358 (the "'358 application"), filed on Apr. 12, 2004 now U.S. Pat. No. 7,628,860, application Ser. No. 11/015,465 (the "'465 application"), filed on Dec. 17, 2004 now U.S. Pat. No. 7,628,861, application Ser. 11/083,586 (the "'586 application"), filed on Mar. 18, 2005 now abandoned, all of which are assigned to the assignee of the present application, and all of which are incorporated herein by reference.

BACKGROUND

Semiconductor fabrication may require carefully synchronized and precisely measured delivery of reactant gases to a process chamber. In an ALD (atomic layer deposition) process, for example, layered films may be created, one atomic layer at a time. Pulses of two or more precursor gases may be sequentially delivered to a process chamber maintained under vacuum. Each precursor gas may flow over a substrate surface to form an adsorbed monolayer on the surface. A second precursor gas may then be introduced into the chamber (after purging the chamber of the first precursor gas), and may react with the first precursor to from a monolayer of the desired thin film via a self-limiting surface reaction. A desired film thickness may be obtained by repeating the deposition cycle as necessary. The film thickness may be controlled to atomic layer accuracy by counting the number of deposition cycles. Likewise, pulsed deposition systems other than ALD processes may require a precisely measured delivery of pulses of gases to process chambers.

To obtain a high level of performance in an ALD process, or in other pulsed deposition processes, the delivery of pulsed mass flow of precursor gases into the semiconductor processing chambers may have to be measured and monitored, in a highly reliable and accurate fashion. ALD control techniques that are based on flow and pressure control may tend to be imprecise, due to various timing inaccuracies at the timescale of interest (milliseconds). Also, these techniques do not control total dose, but rather control flow or pressure, which can lead to significant dose variability due to temperature and timing effects.

It is desirable that highly repeatable and precise quantities of gases be delivered, for use in ALD processes and other semiconductor manufacturing processes. A method and system for actually measuring the amount of gas flowing into the process chamber, and for precisely delivering a desired number of atoms of precursor during each pulse, are desirable.

SUMMARY

An apparatus includes a pulsed gas delivery device configured to deliver a gas in one or more pulses, a sensor coupled to the pulsed gas delivery device, and a controller. The sensor is configured to respond to a presence or an absence of gas delivery by the gas delivery device. The controller is configured to determine, from the response of the sensor, the quantity of the gas delivered by the pulsed gas delivery device.

A method of monitoring with a sensor a delivery of a gas by a gas delivery device includes generating optical radiation at a spectral range that includes an absorption frequency of the gas, and transmitting the optical radiation through a receptacle into which the gas delivered by the gas delivery device has been received. The method further includes detecting an intensity of the optical radiation after transmission of the optical radiation through the gas in the receptacle. The method further includes measuring a quantity of the gas delivered by the gas delivery device by determining, from the detected intensity, an amount of absorption of the optical radiation by the gas in the receptacle.

A method of monitoring delivery of a gas by a pulsed gas delivery device includes coupling to the pulsed gas delivery device a sensor configured to respond to a presence or an absence of gas delivery by the gas delivery device. The method further includes determining, from the response of the sensor, the quantity of the gas delivered by the pulsed gas delivery device.

DETAILED DESCRIPTION

A system and method are described for precisely monitoring gas delivery by pulsed gas delivery systems. In overview, the system may include a pulsed gas delivery device configured to deliver a gas in one or more pulses, a sensor coupled to the pulsed gas delivery device, and a controller. The sensor may be configured to respond to a presence or an absence of gas delivery by the gas delivery device. The controller may be configured to determine, from the response of the sensor, the quantity of gas delivered by the pulsed gas delivery device.

Figure 1A:
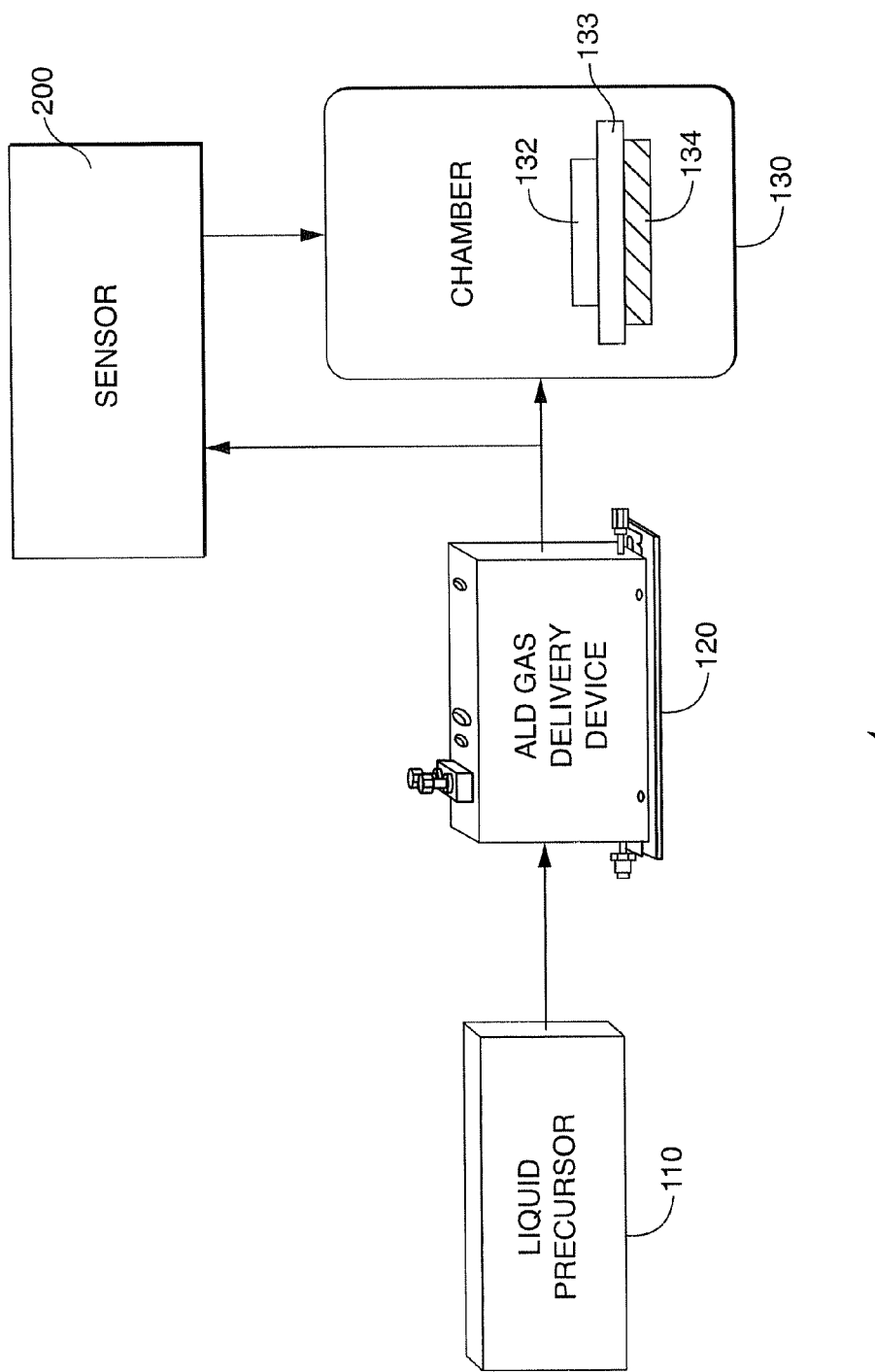
FIG. 1A is a schematic block diagram of one embodiment of a pulsed gas delivery system.

In one embodiment, illustrated in FIG. 1A, the sensor may be an optical sensor, and the pulsed gas delivery device may be part of an ALD (atomic layer deposition) system. FIG. 1A is a schematic block diagram of a pulsed gas delivery system 100 for atomic layer deposition, and an optical sensor 200 used to monitor gas delivery in the ALD system 100. While the embodiment illustrated in FIG. 1A shows an ALD system, it should be understood that the techniques described in this disclosure are applicable to pulsed deposition systems other than ALD systems, and that different embodiments may involve different pulsed deposition systems.

In overview, the ALD system 100 may include: a liquid precursor source 110; an ALD gas delivery device 120; and a process chamber 130. The source 110 may supply liquid precursor to the ALD gas delivery device 120. The ALD gas delivery device 120 may deliver the precursor gases to the processing chamber 130 in a sequence of pulses. The processing chamber 130 may house at least one semiconductor substrate 132, that is being exposed to the precursor gases. Exemplary ALD systems are described in the '358 application, the '465 application, and the '586 application, all of which are incorporated herein by reference.

The ALD gas delivery device 120 may include a vaporizer (not shown), which vaporizes the liquid precursor supplied by the source 110 to generate therefrom precursor gases. In the illustrated embodiment, the ALD gas delivery device 120 may be housed in an integrated heater/vaporizer module, although in some other embodiments, the heater and the vaporizer may be housed in separate modules. The liquid may first be metered from the source 110 by a liquid mass flow controller (not shown), which may be a separate device, or may be combined with the vaporizer into an integrated unit.

The metered liquid may then be vaporized by the vaporizer, thereby forming the precursor gases for the ALD process.

ALD reactions may typically be carried out in a temperature range from about the 200 degrees Celsius to about 400 degrees Celsius. The atomic layer deposition process is based on alternately exposing the substrate 132 to pulses of highly reactive precursor gases. Using pulses of gases, thin films are deposited, one atomic layer at a time, allowing for extremely high uniformity and precise thickness control. During each pulse, a self-limiting gas-solid surface reaction occurs. In a typical ALD process deposition cycle, each of two or more of the precursor or reactant gases is introduced sequentially into the process chamber 130, so that no gas phase intermixing occurs. A monolayer of a first reactant gas is adsorbed onto the substrate surface. Excess first reactant is pumped out, typically with the aid of an inert purge gas. A second reactant is introduced into the process chamber 130, and reacts with the first reactant to form a monolayer of the desired thin film, via a self-limiting surface reaction. This self-limiting reaction ends once the first reactant fully reacts with the second reactant. Excess second reactant is again pumped out, typically with the aid of an inert purge gas. A desired film thickness is obtained by repeating the deposition cycle as necessary.

ALD precursor gases may vary greatly depending on application. New precursors continue to be developed and tested for different substrates and deposition film requirements. Three common precursors are $Al(CH_3)_3$ ($Al_2O_3$ deposition film), $HfCl_4$ ($HfO_2$ deposition film), and $ZrCl_4$ ($ZrO_2$ deposition film). The oxygen precursor for each of these gases is typically $H_2O$, or $O_2$ or $O_3$. Other film types that may be deposited via ALD or CVD techniques include Ni, W, $SiO_2$, $Ta_2O_5$, TaN, $TiO_2$, WN, ZnO, $ZrO_2$, WCN, Ru, Ir, Pt, RuTiN, Ti, Mo, ZnS, $WN_xC_y$, HfSiO, $La_xCa_yMnO_3$, $CuInS_2$, $In_2S_3$, HfN, TiN, Cu, $V_2O_5$, and SiN. It should be noted, however, that the present disclosure is not limited to use with any particular precursor or process.

The processing chamber 130 may typically be maintained under vacuum. The substrate 132 housed within the processing chamber 130 typically resides atop a support or chuck 133. A heater 134 may be coupled to the chuck 133 to heat the chuck 133 and the substrate 132. The chamber environment may be brought up to meet desired parameters. For example, the temperature of the substrate may be increased in order to perform atomic layer deposition.

Figure 1B:
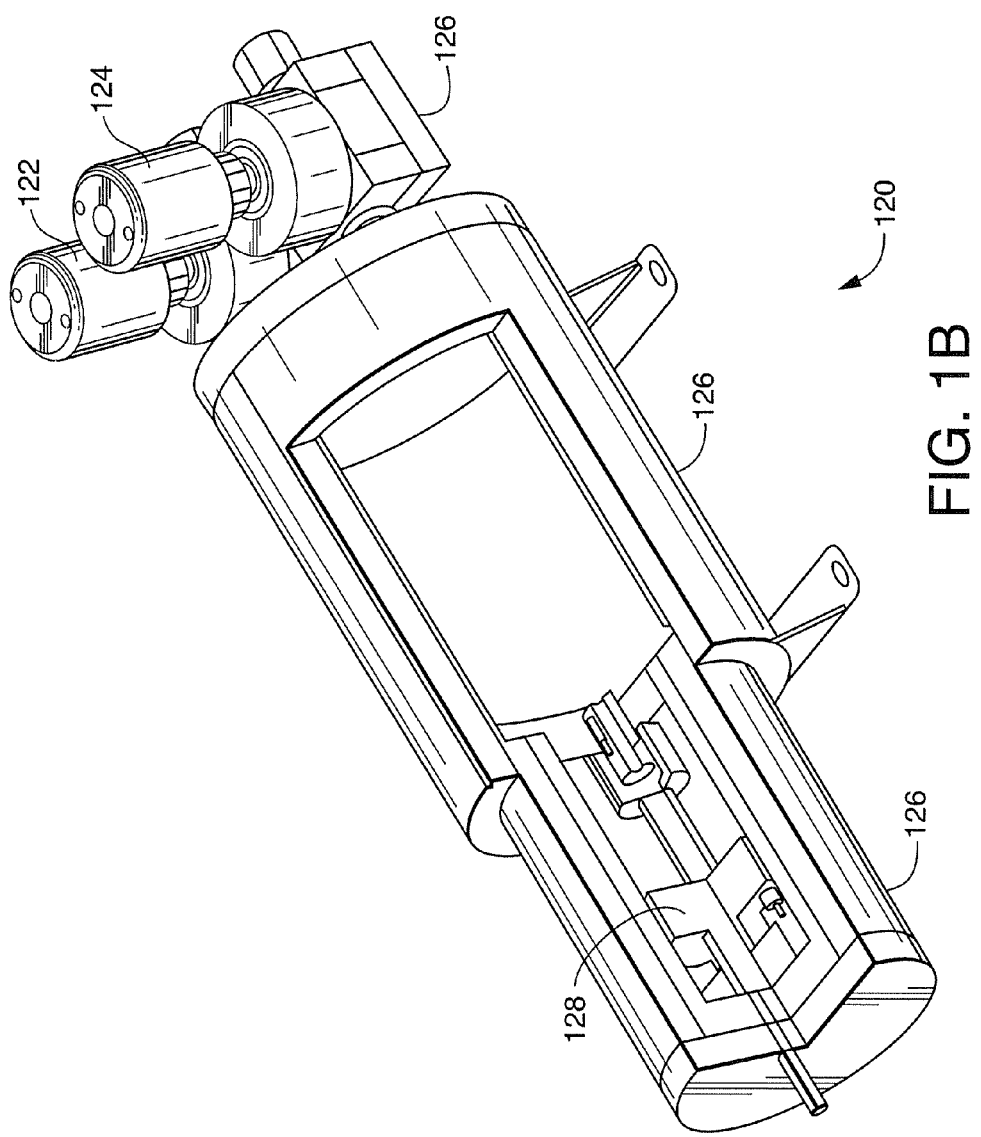
FIG. 1B further illustrates a gas delivery device in the pulsed gas delivery system shown in FIG. 1A.

FIG. 1B provides a cross-sectional view of the ALD gas delivery device 120. In the illustrated embodiment, the ALD gas delivery device 120 is a pulsed delivery device that delivers pulses of gases into the process chamber 130 illustrated in FIG. 1A. In overview, the illustrated embodiment of the ALD gas delivery device 120 may include: gas delivery on-off valves 122; purge valves 124; one or more heaters 126; and a pressure transducer 128.

As explained earlier, liquid precursor from the source 110 may be vaporized by a vaporizer, before being delivered to a holding container. The holding container may be heated to an appropriate temperature by the heaters 126. In the illustrated embodiment, the heaters may be 6-zone heaters, although the disclosure is not limited to 6-zones, of course.

The pressure transducer 128 may be configured to provide measurements of pressure within the process chamber 130. An example of a suitable pressure transducer 128 for use in the ALD gas delivery device 120 may be the Baratron brand pressure transducer available from the assignee of the present disclosure, MKS Instruments of Andover, Mass.

The on-off type gas valves 122 may be used to deliver a desired amount of precursor gas from the heated holding container into the processing chamber 130. In other words, the pulses of precursor gases delivered into the processing chamber 130 may be controlled using the gas delivery on-off valves 122 and the purge valves 124. The valves 122 and 124 may be opened for predetermined periods to deliver a desired amount of precursor gases and purge gases, respectively, into the processing chamber 130. The valves 122 and 124 may be field-replaceable valves.

The ALD deposition process may require very precisely measured and controlled quantities of precursor gases to be delivered to the process chamber 130. The delivery of precursor gases should thus be monitored and controlled in a highly accurate and repeatable manner. Likewise, other types of pulsed deposition processes similarly require precise and accurate monitoring and control of gas delivery. Flow and pressure mode techniques, in which the mass flow of the gases is estimated by monitoring pressure and valve on/off time periods, tend to be imprecise due to various timing inaccuracies at the timescale of interest (i.e. milliseconds). These techniques may not control total dose, i.e. may not measure the actual mass of gas flowing into the process chamber 130, but instead may control flow or pressure. This may lead to significant dose variability, due to temperature and timing effects.

Referring back to FIG. 1A, a sensor 200 may be used to monitor in real time gas delivery from the ALD gas delivery device 120. The sensor 200 may be placed between the ALD gas delivery device 120 and the process chamber 130. The sensor 200 may be an optical sensor capable of measuring gas concentration in each pulse delivered by the gas delivery device 120, by detecting the reduction in optical radiation due to absorption of the optical radiation by the delivered gas. The optical sensor may, for example, be an IR (infrared) sensor configured to detect infrared radiation, and to measure gas concentration in each pulse by detecting the reduction IR radiation due to absorption of the IR radiation by the gas. Alternatively, the optical sensor may be a sensor configured to detect optical radiation outside of the IR frequency range, including but not limited to a UV (ultraviolet) sensor, or a sensor configured to detect visible light.

The sensor 200 may allow for a precise delivery of a desired number of atoms of the precursor gas, for each pulse. The sensor 200 may allow for tighter control, since the variations in temperature and pressure can be fully taken into account.

Figure 2:
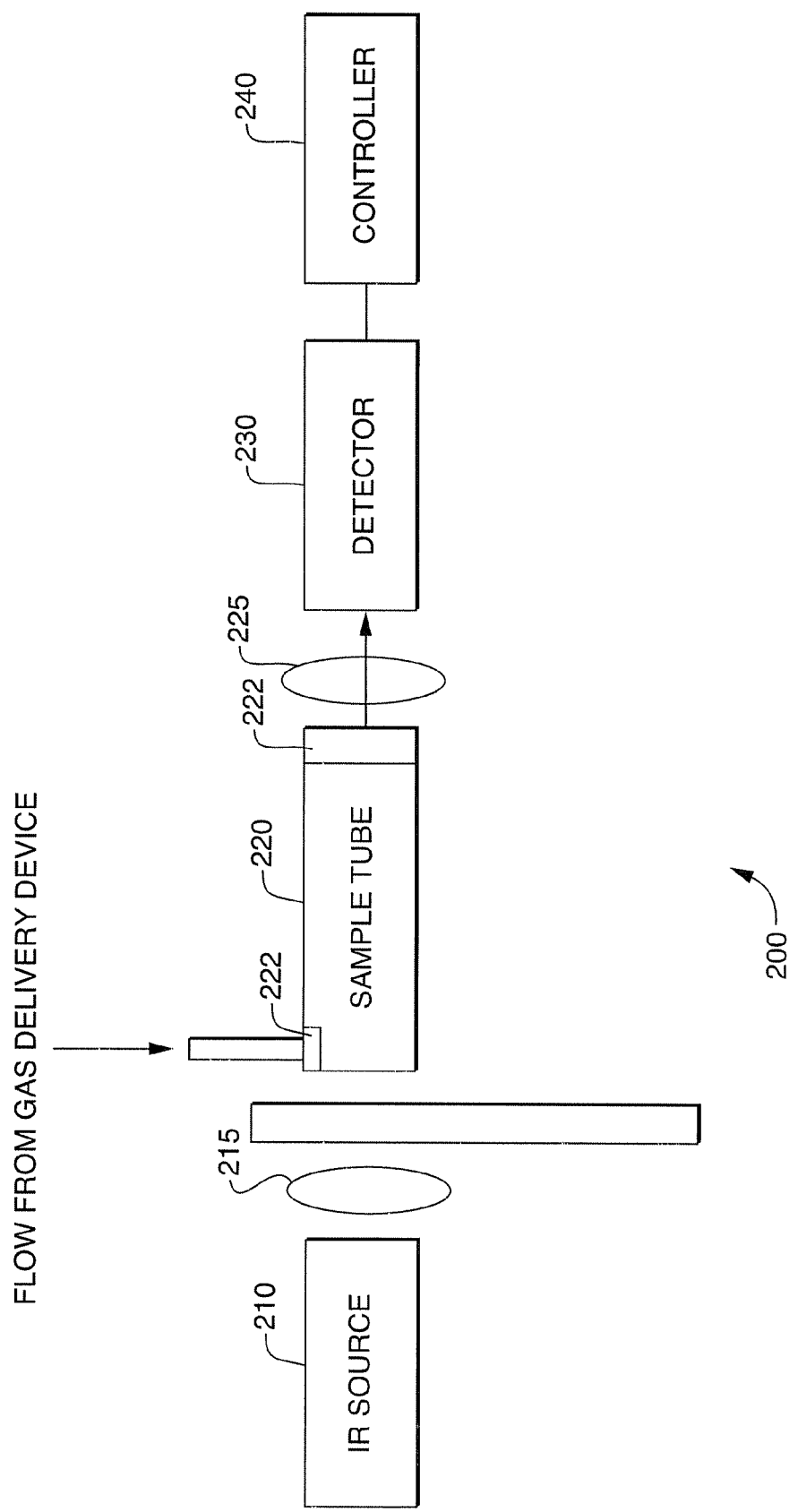
FIG. 2 is a conceptual diagram of an optical sensor for monitoring gas delivery.

FIG. 2 is a conceptual diagram of the optical sensor 200 used in the ALD system (shown in FIG. 1A) to monitor and control gas delivery during the ALD process. Although FIG. 2 shows an optical sensor 200, other embodiments may use other types of sensors that are capable of measuring gas concentration in each pulse delivered by the gas delivery device 120, by detecting a signal that is relative to the concentration or partial pressure of the delivered gas. These sensors may include, but are not limited to: acoustic sensors; photoacoustic sensors; mass spectrometers; fluorescence spectrometers; and electrolytic sensors.

While an IR (infrared) optical sensor is shown in FIG. 2 that is configured to generate and detect IR radiation, other embodiments may use optical sensors designed for optically absorbing gases that fall in spectral ranges other than infrared, including but not limited to the visible or UV spectral ranges.

In overview, the optical sensor 200 includes: a source 210 of radiation configured to generate optical radiation at a spectral range that includes an absorption spectrum of the precursor gas being delivered by the ALD gas delivery device 120 (shown in FIGS. 1A and 1 B); a detector 230 capable of detecting the optical radiation generated by the source 210; and a receptacle or sample tube 220 that is open to the precursor gas to be detected, and that provides an optical path between the detector 230 and the source 210. The precursor gas flows into the sample tube 220 from the gas delivery device 120.

The detector 230 is configured to detect the specific frequency (or frequencies) and/or spectral range (or ranges) of the IR radiation, generated by the source 210, that reaches the detector 230 after being transmitted through the precursor gas in the sample tube 220, and to generate one or more detector signals representative of the detected intensity.

A controller 240 is coupled to the detector 230, and includes signal processing circuitry configured to measure the quantity of the delivered gas by processing the detector signals. The controller 240 determines, from the detected intensity of IR radiation, the amount of IR radiation that was absorbed by the gas in the sample tube 220. When the gas in the sample tube 220 absorbs energy from the optical radiation generated by the source 210, the detector 230 detects less intensity than it would have if the radiation from the source 210 had reached the detector 230 at full intensity. This reduction in radiation allows the concentration of the delivered gas to be measured. In one embodiment, the reduction in radiation may be directly proportional to the absorbance. In other embodiments, different algebraic methods can be used to derive the reduction in radiation.

In the embodiment of the optical sensor illustrated in FIG. 2, the source 210 generates IR light at a spectral range that includes the absorption spectrum of the precursor gases delivered by the gas delivery device 120. If only IR light having an exactly matching absorption frequency hits the detector, then any absorption by the precursor gas will be detected. Because most sources produce radiation over a broad spectrum, and most detectors detect radiation over a broad spectrum, energy from the source 210 should be limited so that the detector 230 mainly sees photons that will be absorbed by the precursor gas in the sample tube 220.

The optical sensor 200 therefore typically includes a wavelength selection device 225. For example, the wavelength selection device 225 may be an IR narrowband filter 225 at an appropriate frequency, configured to selectively transmit light of an appropriate desired frequency onto the detector. The wavelength selection device 225 may also include more than one IR narrowband filter 225 operative at the appropriate frequencies. The wavelength selection device 225 may also be operative at one or more IR bands that incorporate the appropriate frequencies. Alternatively, the wavelength selection device 225 may be one or more of the followings: a grating, a prism, an interferometer, a laser, a frequency-specific diode, and an acoustic-optic filter.

The sample tube 229 for the precursor gases delivered by the delivery device 120 may have a radiation-transmissive window 222 that allow transmission of the IR light from the source 210 onto the sample tube 220, and from the sample tube 220 onto the detector 230. In one embodiment, the sample tube 220 may be part of the ALD processing chamber 130 (shown in FIG. 1A). A focusing mirror or lens 215 may be provided, that focuses the light generated by the source 210 onto the sample tube 220.

When IR light generated by the source 210 strikes a gas molecule in the sample tube 220, as the IR light is being transmitted through the sample tube 220, energy from one or more photons of the IR light may be absorbed by the gas molecule, if the photon's energy precisely matches a characteristic energy state (vibrational, rotational, etc.) of the gas molecule. Each gas molecule exhibits a very specific set of absorption wavelengths, which depend on the strength of the chemical bonds between the atoms that make up the gas molecule.

In order to reduce sensor drift and calibration drift, the IR light source 210 may be modulated in, time, so as to provide a drift free signal that can be monitored. The source 210 may be modulated at a rate of about 10 Hz, or faster. In some embodiments, the source 210 may be modulated at a rate of up to 100 Hz, or faster. The ALD pulses may be about 1 second in duration. These parameters may determine the sensitivity required, and the type of detector required, to make the necessary measurements. If 10 Hz is fast enough, the detector 230 may be configured to be a $LiTaO_3$ detector, by way of example. If a faster detector is required, the detector 230 may include, but is not limited to, one or more of the following detectors: a DTGS detector, a PbS detector, a PbSe detector, or an MCT detector.

The controller 240 may include circuitry that allows the sensor 200 to self-zero before or after a deposition process or between deposition pulses while the deposition gases are not flowing. The controller may be configured to determine whether gas delivery by the gas delivery device is at a zero, and if so, to reset the sensor to report the zero. The controller may also include calibrating circuitry that may be configured to initially calibrate the optical sensor 200 with a known amount of gas or reference material, then to re-set the calibration of the sensor 200 by using a known gas quantity or the reference material.

As mentioned earlier, although ALD gas delivery has been described, the techniques described in this disclosure are applicable to any pulsed gas delivery systems, and are not limited to ALD systems.

The controller 240 may be configured to monitor the delivery of the gas in real time, by generating and transmitting one or more control signals that adaptively adjust the quantity of gas that is being delivered to a desired quantity, in response to the detected intensity indicated by the detector signals. The controller 240 may determine and monitor the amount of gas delivered during each ALD pulse, i.e. may measure and monitor the amount of ALD precursor delivered from the ALD gas delivery device to the chamber 130.

The controller 240 may also determine and monitor the total integrated quantity of gas that is delivered during a time period encompassing a plurality of ALD pulses. For example, the controller 240 may measure and monitor the integrated amount of ALD precursor per ALD cycle. The ALD system 100 (shown in FIG. 1A) may thus be monitored with an absolute concentration method. The ALD system 100 may also be monitored with an algebraic combination of signal (or band) intensities or areas to either provide absolute concentrations or discriminate between events to provide an optimal final product. The controller 140 may provide real-time feedback for the ALD delivery system, with about a 1% measurement precision and accuracy, and at a 10 Hz or faster analysis rate.

Alternatively, a separate monitoring device (not shown) may be provided that is configured to monitor delivery of the gas in real time, by generating and transmitting one or more control signals that adaptively adjust gas delivery to a desired quantity.

The controller 240 may be configured to monitor the drift of delivered gases by the ALD system. The controller 240 may also be configured to monitor the rise time and fall time of the ALD gas delivery device. The controller 240 may also be configured to monitor an absolute zero of the ALD gas delivery device 120. The controller 240 may also be configured to monitor any malfunctioning of the valves 122 and or

124, so as to determine if and when the valves need to be changed, and whether the gas delivery device 120 requires maintenance. The controller 240 may be configured as a Statistical Process Control system, monitoring and/or controlling multiple contributions to the ALD process.

The approach described above allows for adaptive control. In other words, the controller 240 adaptively controls the delivery of the gas to a desired quantity, by generating appropriate control signals indicating the desired amount that should be delivered, in response to detector signals that measure the amount of gas contained in the pulse being delivered.

The approach also allows the controller 240 to determine if and when the valves 122 and/or 124 are not functioning correctly, for example if the valves are bleeding, or if the valves fall outside of open and close tolerances. Because the sensor is extremely sensitive and allows for a precise delivery of a desired number of atoms of precursor for each pulse, the controller 240 can be configured to detect whenever at least one of the valves bleed gas in a closed or "off" state.

In this way, the approach described above provides for closed loop control for delivery of critical reactants into the ALD chamber, where consistent and precise delivery of precursors are critical to the quality and performance of the deposited film layers. The method and system described above allows for a precise delivery of a desired number of atoms of precursor for each pulse. The sensor and controller described above allows for a tighter control of the ALD process, fully taking into account the variations in temperature and pressure. ALD process variability, cause for example by valve to valve variation, valve degradation over time, and/or variation of delivery conditions, can be reduced.

In sum, a method and apparatus have been described that allows ALD systems to be monitored and controlled, with an absolute concentration method. The optical sensor described above allows the delivery of the ALD gas to be monitored to within a few % of read, i.e. 100 ppm plus or minus 2 ppm. The sensor described above may also be used in any gas delivery system, other than ALD systems, that has a pulsed delivery. The sensor may also be used in conjunction with endpoint devices, since these process are usually fairly short in duration.

While certain embodiments have been described of an apparatus and method for pulsed deposition monitoring and control, it is to be understood that the concepts implicit in these embodiments may be used in other embodiments as well. The protection of this application is limited solely to the claims that now follow.

In these claims, reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference, and are intended to be encompassed by the claims. Moreover, nothing disclosed herein is intended to be dedicated to the public, regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An apparatus comprising:
(A) a process chamber;
(B) a pulsed gas delivery device configured to deliver into the process chamber a gas, in one or more pulses, wherein the pulsed gas delivery device comprises a delivery chamber;
a first valve controlling gas flow into the delivery chamber;
a second valve controlling gas flow out of the delivery chamber;
a pressure transducer providing measurements of pressure within the delivery chamber;
a controller connected to the valves and the pressure transducer, wherein the controller is configured and arranged to
(i) receive a desired mass flow setpoint from an input device;
(ii) close the second valve;
(iii) open the first valve;
(iv) receive chamber pressure measurements from the pressure transducer;
(v) close the first valve when pressure within the delivery chamber reaches a predetermined level;
(vi) wait a predetermined waiting period to allow the gas inside the delivery chamber to approach a state of equilibrium;
(vii) open the second valve at time=$t_0$;
(viii) calculate a value of the total mass delivered from the delivery chamber when the second valve is open and as a function of temperature and pressure within the delivery chamber; and
(ix) close the second valve at time=t* when the calculated value of total mass delivered from the delivery chamber equals the desired mass flow setpoint, wherein t* is from about 100 milliseconds to about 500 milliseconds;
(C) an optical sensor disposed between the pulsed gas delivery device and the process chamber;
wherein the optical sensor includes:
an optical source configured to generate optical radiation at a spectral range that includes an absorption frequency of the gas, wherein the optical source comprises a modulated source configured and arranged to modulate the intensity of the generated optical radiation;
a receptacle for the gas;
a wavelength selecting device including a narrowband filter configured to selectively transmit, from the receptacle to a detector, a desired narrowband bandwidth of the optical radiation in the receptacle; and
an optical detector configured to detect an intensity of the optical radiation that reaches the detector from the source after transmission of the optical radiation through the gas in the receptacle;
wherein the controller is further configured to determine and monitor, based on the response of the optical sensor, a quantity of the gas that is being delivered by the pulsed delivery device at that location, the controller further configured to monitor the delivery of the gas in real time by generating and transmitting one or more control signals that adaptively adjust the number of pulses and the quantity of gas being delivered by the pulsed gas delivery device to a desired number and quantity, the controller further configured to measure a total integrated amount of the gas delivered into the process chamber by the pulsed gas delivery device during a time period that encompasses a plurality of the pulses, the controller further configured to determine the quantity of the gas delivered by the gas delivery device by deriving, from the intensity detected by the detector, an amount of absorption of the optical radiation by the gas in the receptacle.

2. The apparatus of claim 1, wherein the optical sensor is further configured to generate one or more detector signals representative of the detected intensity of the optical radiation, and wherein the controller is further configured to measure the quantity of the delivered gas by processing the detector signals.

3. The apparatus of claim 1, wherein the controller further comprises a monitoring device configured to monitor delivery of the gas in real time, by generating and transmitting a control signal that adaptively adjusts gas delivery to a desired quantity.

4. The apparatus of claim 3, wherein the controller is further configured to monitor at least one of a rise time and a fall time of the pulsed gas delivery device.

5. The apparatus of claim 3, wherein the controller is further configured to monitor an absolute zero of the pulsed gas delivery device.

6. The apparatus of claim 1, wherein the controller is further configured to determine whether gas delivery by the gas delivery device is at a zero, and if so, to reset the sensor to report the zero.

7. The apparatus of claim 6, wherein the controller is further configured to reset the sensor to report the zero between each one of the pulses.

8. The apparatus of claim 1,
wherein the controller is configured to determine and monitor a quantity of the gas that is delivered during each one of the pulses, in addition to the total integrated amount of the gas that is delivered during the time period that encompasses a plurality of the pulses.

9. The apparatus of claim 1, wherein the gas delivery device comprises an ALD (atomic layer deposition) gas delivery device, the process chamber comprises an ALD process chamber, and the apparatus comprises an ALD system; and wherein the ALD gas delivery device is configured to deliver at least one ALD precursor gas to the ALD process chamber.

10. The apparatus of claim 9, wherein the controller is further configured to determine and monitor a concentration of the ALD precursor gas delivered from the ALD gas delivery device to the ALD process chamber during each pulse, and
wherein the controller is further configured to determine and monitor an integrated amount of the ALD precursor gas delivered during a cycle of the ALD system that includes the ALD gas delivery device, the ALD process chamber, and a source of liquid precursor for the ALD gas delivery device.

11. The apparatus of claim 10, wherein the controller is further configured to monitor a variation in gas delivery of the ALD system.

12. The apparatus of claim 1, wherein the source of radiation is modulated at a rate greater than about 10 Hz.

13. The apparatus of claim 1, wherein the wavelength selecting device further comprises at least one of:
a grating;
a prism;
a laser;
a frequency specific diode;
an interferometer; and
an acoustic optic filter.

14. The apparatus of claim 1, wherein the detector comprises a photosensitive detector.

15. The apparatus of claim 14, wherein the photosensitive detector comprises at least one of:
a $LiTaO_3$ detector;
a PbS detector;
a PbSe detector;
a DTGS detector; and
an MCT detector.

16. The apparatus of claim 1, wherein the receptacle includes at least one of: a radiation-transmissive window that allows transmission of the optical radiation from the source into the receptacle; and a radiation-transmissive window that allows transmission of the optical radiation from the receptacle onto the detector.

17. The apparatus of claim 1, wherein the optical sensor comprises an IR (infrared) radiation sensor, the radiation source comprises an IR source, the optical radiation comprises IR radiation, the absorption frequency comprises an IR absorption frequency, and the detector comprises an IR detector.

18. The apparatus of claim 1, wherein the optical sensor comprises at least one of: a UV (ultraviolet) radiation sensor including a source of UV radiation, and a UV detector; and
a visible light sensor including a source of visible light, and a detector configured to detect visible light.

19. The apparatus of claim 1, wherein the controller is further configured to determine whether the gas delivery device requires maintenance.

20. The apparatus of claim 19,
wherein the controller is further configured to determine whether the first or second valves are malfunctioning.

21. The apparatus of claim 20, wherein the apparatus further comprises a pressure transducer configured to measure a pressure in the process chamber, and wherein the maintenance comprises maintenance of at least one of:
the pressure transducer;
the one or more valves; and
a software in the controller.

22. The apparatus of claim 20, wherein the controller is further configured to monitor a gas bleed through the gas delivery device when at least one of the valves is in the off-state.

23. The apparatus of claim 1, wherein the radiation sensor comprises at least one of:
an acoustic radiation sensor;
a photoacoustic radiation sensor; and
a fluorescent radiation sensor.

* * * * *